United States Patent [19]
Nishi

[11] Patent Number: 5,069,753
[45] Date of Patent: Dec. 3, 1991

[54] METHOD FOR MAKING DRY SHEET-LIKE SAMPLE OF SOLID PARTICLES FROM A SUSPENSION

[75] Inventor: Masahiro Nishi, Shizuoka, Japan

[73] Assignee: Kyoritsu Electric Corporation, Shizuoka, Japan

[21] Appl. No.: 496,702

[22] Filed: Mar. 21, 1990

[30] Foreign Application Priority Data

| Jul. 19, 1989 | [JP] | Japan | 1-186374 |
| Jul. 19, 1989 | [JP] | Japan | 1-186375 |
| Jul. 19, 1989 | [JP] | Japan | 1-186376 |
| Jul. 19, 1989 | [JP] | Japan | 1-186377 |
| Jul. 19, 1989 | [JP] | Japan | 1-186378 |
| Jul. 19, 1989 | [JP] | Japan | 1-186379 |

[51] Int. Cl.$^5$ .............. D21F 13/00; G01N 5/04
[52] U.S. Cl. .................... 162/49; 73/63; 73/61 R; 162/198; 162/263
[58] Field of Search ............ 162/49, 198, 252, 258, 162/263, 398, 399, 407, 396; 73/61 R, 63, 866, 433

[56] References Cited

U.S. PATENT DOCUMENTS

| 3,152,036 | 10/1964 | Box et al. | 162/258 |
| 3,585,106 | 6/1971 | Sepall et al. | 162/263 |
| 4,323,426 | 4/1982 | Cowan et al. | 162/398 |
| 4,662,991 | 5/1987 | Karna et al. | 162/49 |
| 4,708,011 | 11/1987 | Rantakorpi et al. | 73/63 |

FOREIGN PATENT DOCUMENTS 1291143 11/1989 Japan.

Primary Examiner—Karen M. Hastings
Attorney, Agent, or Firm—Lowe, Price, LeBlanc & Becker

[57] ABSTRACT

In a method and apparatus for making a dry sheet-like sample of solid particles from a suspension, a part of the suspension is sampled by a sampling unit as it flows through a pipe or while it is retained in a storage tank, then the sampled suspension is stirred by supplying a compressed air and then dewatered by filtration with vacuum, thereby forming a wet sheet-like intermediate sample of solid particles deposited on a filter. Subsequently, the filter and the intermediate sample deposited thereon are conveyed by an overturning conveyor unit to a drying station while being turned upside down, thereafter intermediate sample is removed from the filter by a sample removing unit, and finally, the wet sheet-like intermediate sample is dried with heat and pressure whereby a dry sheet-like final sample is obtained.

1 Claim, 20 Drawing Sheets

METHOD FOR MAKING DRY SHEET-LIKE SAMPLE OF SOLID PARTICLES FROM A SUSPENSION

BACKGROUND OF THE INVENTION

The present invention relates to a method and apparatus for making a dry sheet-like sample of solid particles from a suspension. It also relates to a method and apparatus for measuring the pulp concentration of a dilute fiber suspension or pulp liquor.

In the paper making industry, control of the pulp concentration is a very important matter to a stable paper-making operation and a uniform quality of paper pulp obtained.

The pulp concentration is a proportion of the oven-dry weight of fiber contents in dilute fiber suspension to the total weight of the dilute fiber suspension which is indicated in terms of weight percent.

According to a conventional practice, the measurement of the pulp concentration is achieved by first manually sampling a part of the dilute fiber suspension into a measuring cup as it flows through a pipe. Then, the total weight of the sampled dilute fiber suspension is measured.

Subsequently, the sampled pulp liquor is squeezed to extract fiber contents which are in turn extended into a wet sheet-like intermediate fiber mat or sample. The intermediate sample is dried by heating within an oven under appropriate heating conditions such, for example, as at 130° C. for 2 hours. Thus, a dry sheet-like final sample or fiber mat is obtained.

The dry final sample is weighed for its oven-dry weight (also known as "absolute dry weight") and a proportion of the oven-dry weight of the dry final sample to the total weight of the dilute fiber suspension is calculated. The pulp concentration is thus obtained.

The conventional measurement of the pulp concentration substantially entirely depends on the manual operation and hence is a time-consuming practice. Due to the manual operation, the measuring accuracy is relatively low.

SUMMARY OF THE INVENTION

With the foregoing drawbacks of the prior art in view, it is an object of the present invention to provide a method and apparatus for making a dry sheet-like sample of solid particles from a suspension automatically and efficiently.

Another object of the present invention is to provide a method and apparatus for measuring the pulp concentration of a dilute fiber suspension in an automated manner and at a high degree of accuracy.

According to a first aspect of the present invention, there is provided a method of making a dry sheet-like sample of solid particles from a suspension, comprising the steps of: (a) sampling a part of the suspension as it flows through a pipe or while it is retained in a storage tank; (b) stirring the thus-sampled suspension by supplying a compressed air to the sampled suspension and then dewatering the stirred suspension by filtration with vacuum, thereby forming a wet sheet-like intermediate sample of solid particles deposited on a filter; (c) conveying the filter and the wet sheet-like intermediate sample deposited thereon to a drying station while turning the filter and the wet sheet-like intermediate sample upside down, and subsequently removing the wet sheet-like intermediate sample from the filter; and (d) thereafter, drying the wet sheet-like intermediate sample with heat and pressure, thereby forming a dry sheet-like final sample.

According to a second aspect of the present invention, there is provided an apparatus for making a dry sheet-like sample of solid particles from a suspension, comprising: (a) a sampling unit including a sampling mechanism having a hopper connected in branched fashion to a main pipe or a storage tank for sampling a part of the suspension as it flows through the main pipe or while it is retained in the storage tank, and a water sprinkling mechanism for sprinkling water against the sampling mechanism and an inside surface of the hopper for removing the suspension adhering to the sampling mechanism and the inside surface of the hopper; (b) a wet sheet-like intermediate sample forming unit including a tank for holding therein the sampled suspension, a filter removably disposed in the tank, means for stirring the sampled suspension held in the tank, and means for dewatering the sampled suspension from the tank to thereby form a wet sheet-like intermediate sample of solid particles deposited on the filter; (c) an overturning conveyor unit for conveying the filter and the wet sheet-like intermediate sample from a position within the tank to a drying station while turning the filter and the wet sheet-like intermediate sample upside down; (d) a sample removing unit for removing the wet sheet-like intermediate sample from the filter; and (e) a dryer unit disposed at the drying station and including upper and lower hot plates relatively movable toward and away from each other to compress the wet sheet-like intermediate sample therebetween for drying the wet sheet-like intermediate sample with heat and pressure, thereby forming a dry sheet-like final sample.

According to a third aspect of the present invention, there is provided a method of measuring the pulp concentration of a dilute fiber suspension, comprising the steps of: (a) sampling a part of the dilute fiber suspension as it flows through a pipe or while it is retained in a storage tank; (b) stirring the thus-sampled dilute fiber suspension by supplying a compressed air to the sampled dilute fiber suspension and then dewatering the stirred dilute fiber suspension by filtration with vacuum, thereby forming a wet sheet-like intermediate sample of solid particles deposited on a filter; (c) conveying the filter and the wet sheet-like intermediate sample deposited thereon to a drying station while turning the filter and the wet sheet-like intermediate sample upside down, and subsequently removing the wet sheet-like intermediate sample from the filter; (d) thereafter, drying the wet sheet-like intermediate sample with heat and pressure, thereby forming a dry sheet-like final sample; and (e) transferring the dry sheet-like final sample to a weighing station and then measuring an oven-dry weight of the dry sheet-like final sample for subsequent calculation of the pulp concentration of the dilute fiber suspension based on the oven-dry weight of the final sample and a total weight of the sampled dilute fiber suspension.

According to a fourth aspect of the present invention, there is provided an apparatus for measuring the pulp concentration of a dilute fiber suspension, comprising: (a) a sampling unit including a sampling mechanism having a hopper connected in branched fashion to a main pipe or a storage tank for sampling a part of the dilute fiber suspension as it flows through the main pipe or while it is retained in the storage tank, and a water sprinkling mechanism for sprinkling water against the sampling mechanism and an inside surface of the hopper for removing the dilute fiber suspension adhering to the sampling mechanism and the inside surface of the hopper; (b) a wet sheet-like intermediate sample forming unit including a tank for holding therein the sampled dilute fiber suspension, a filter removably disposed in the tank, means for stirring the sampled dilute fiber suspension held in the tank, and means for dewatering the sampled dilute fiber suspension from the tank to thereby form a wet sheet-like intermediate sample of solid particles deposited on the filter; (c) an overturning conveyor unit for conveying the filter and the wet sheet-like intermediate sample from a position within the tank to a drying station while turning the filter and the wet sheet-like intermediate sample upside down; (d) a sample removing unit for removing the wet sheet-like intermediate sample from the filter; (e) a dryer unit disposed at the drying station and including upper and lower hot plates relatively movable toward and away from each other to compress the wet sheet-like intermediate sample therebetween for drying the wet sheet-like intermediate sample with heat and pressure, thereby forming a dry sheet-like final sample; (f) a final sample transfer unit for transferring the dry sheet-like final sample from the dryer unit to a weighing station; and (g) a weighing unit disposed at the weighing station for measuring an oven-dry weight of the final sample.

The above and other objects, features and advantages of the present invention will become more apparent from the following description when making reference to the detailed description and the accompanying sheets of drawings in which preferred structural embodiments incorporating the principles of the present invention are shown by way of illustrative example.

DETAILED DESCRIPTION OF THE PREFERRED EMBODIMENT

Figure 3:
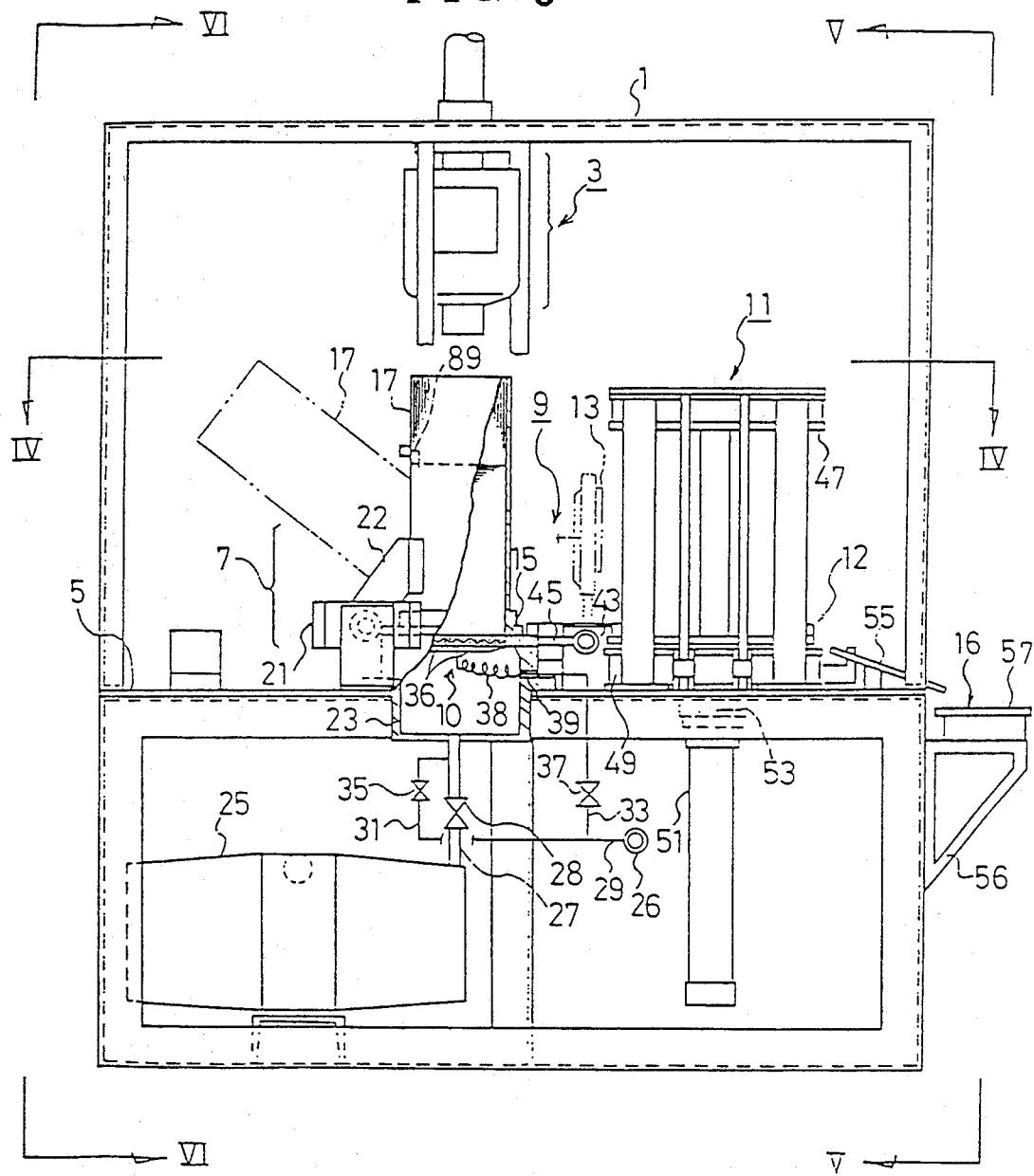
FIG. 3 is a front elevational view of an apparatus for measuring the pulp concentration of a dilute fiber suspension according to the present invention.
Figure 4:
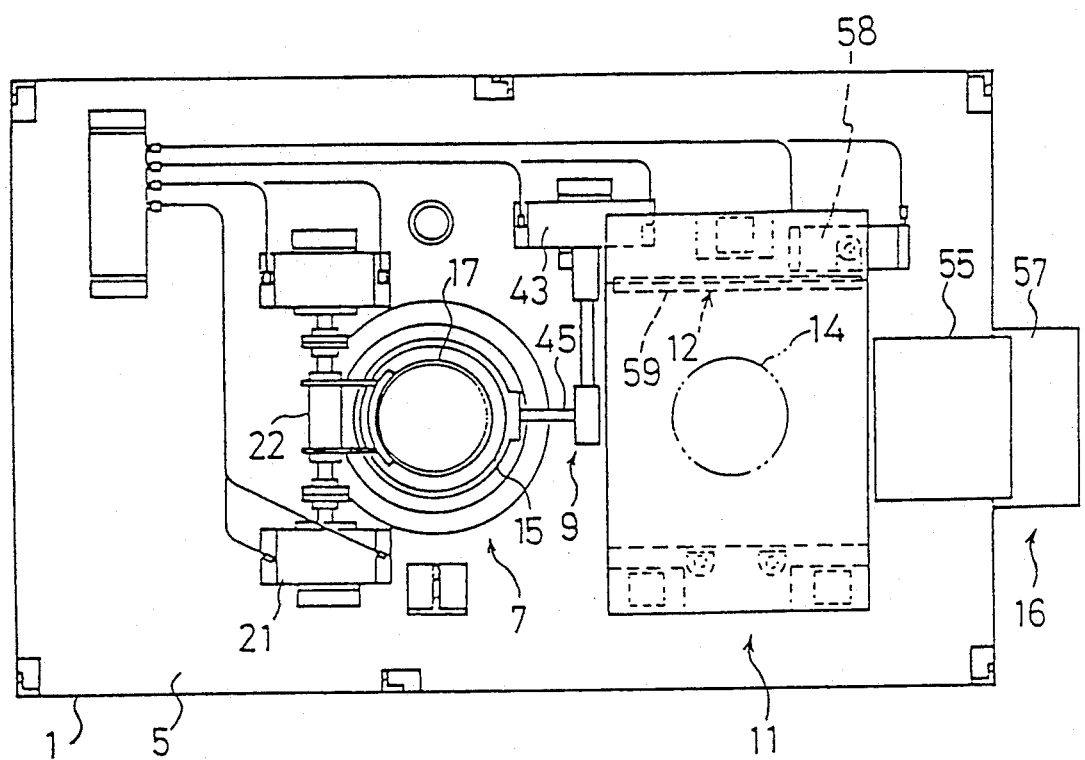
FIG. 4 is a cross-sectional view taken along line IV—IV of FIG. 3.
Figure 5:
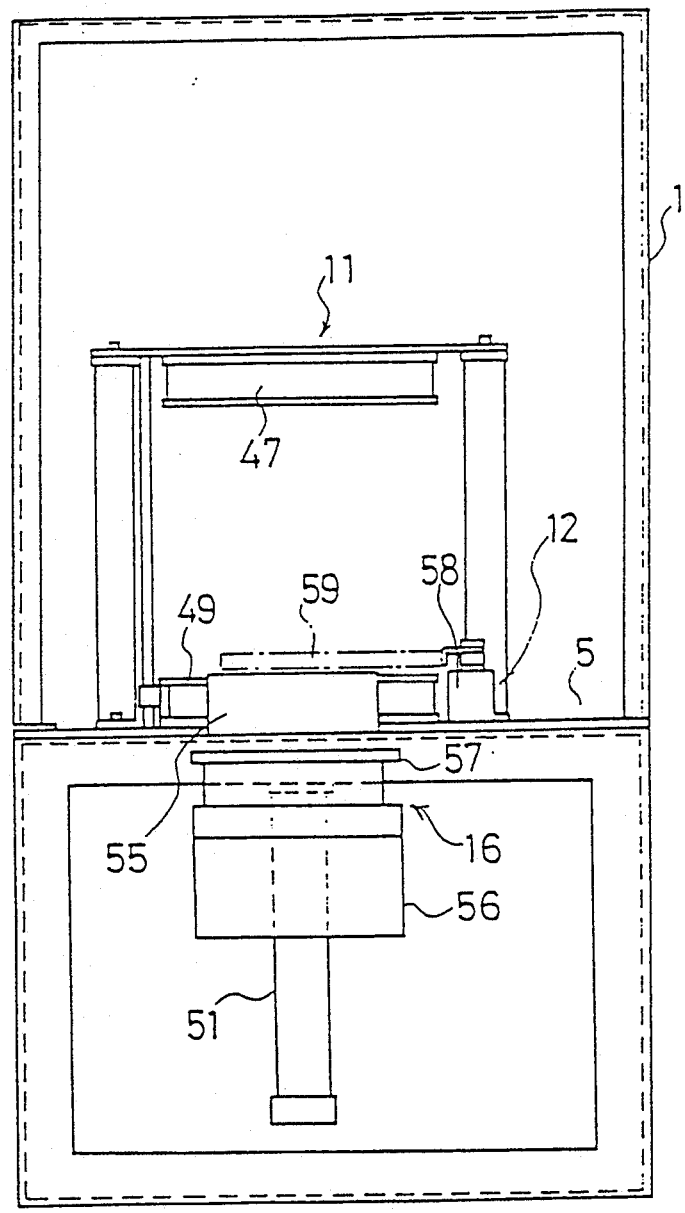
FIG. 5 is a view taken in the direction of the arrows along the line V—V of FIG. 3.

Referring now to the drawings wherein like reference characters designate like or corresponding parts throughout the several views, and more particularly to FIG. 3, there is shown a pulp concentration measuring apparatus embodying the present invention.

The pulp concentration measuring apparatus includes a substantially rectangular frame 1 having an upper portion on which a sampling device or unit 3 is mounted for sampling a predetermined quantity of dilute fiber suspension.

The frame 1 further has a horizontal table 5 disposed in a substantially intermediate position as viewed in the vertical direction. The table 5 supports thereon a wet sheet-like intermediate sample forming device or unit 7 incorporating a stirring means and a dewatering means, an overturning conveyor device or unit 9 for transferring the wet intermediate sample while turning the same upside down, a sample removing device or unit 10 associated with the overturning conveyor unit 9 for removing the wet sheet-like intermediate sample from a filter, a dryer device or unit 11 for drying the wet sheet-like intermediate sample with heat and pressure, thereby forming a dry sheet-like final sample, a transfer device or unit 12 for transferring the dry sheet-like final sample to a weighing station, and a weighing device or unit 16 for weighing an oven-dry weight of the dry sheet-like final sample at the weighing station.

The dilute fiber suspension collected by the sampling unit 3 is supplied to the wet sheet-like intermediate sample forming unit 7 where a wet sheet-like intermediate sample 13 of fibrous materials is formed. The thus-formed wet sheet-like intermediate sample 13 is transferred by the overturning conveyor unit 9 to the dryer unit 11 at which it is removed from a filter by the sample removing unit 10.

Then, the wet sheet-like intermediate sample 13 is dried with heat and pressure by the dryer unit 11. A dry sheet-like final sample 14 is thus obtained. The final sample 14 is transferred by the transfer unit 12 to a weighing position where it undergoes subsequent measurement of its oven-dry weight. A proportion of the oven-dry weight of the final sample 14 to the total weight of the sampled dilute fiber suspension is calculated to obtain the pulp concentration of the dilute fiber suspension.

The construction of the respective units will be described below in greater detail.

Figure 11:
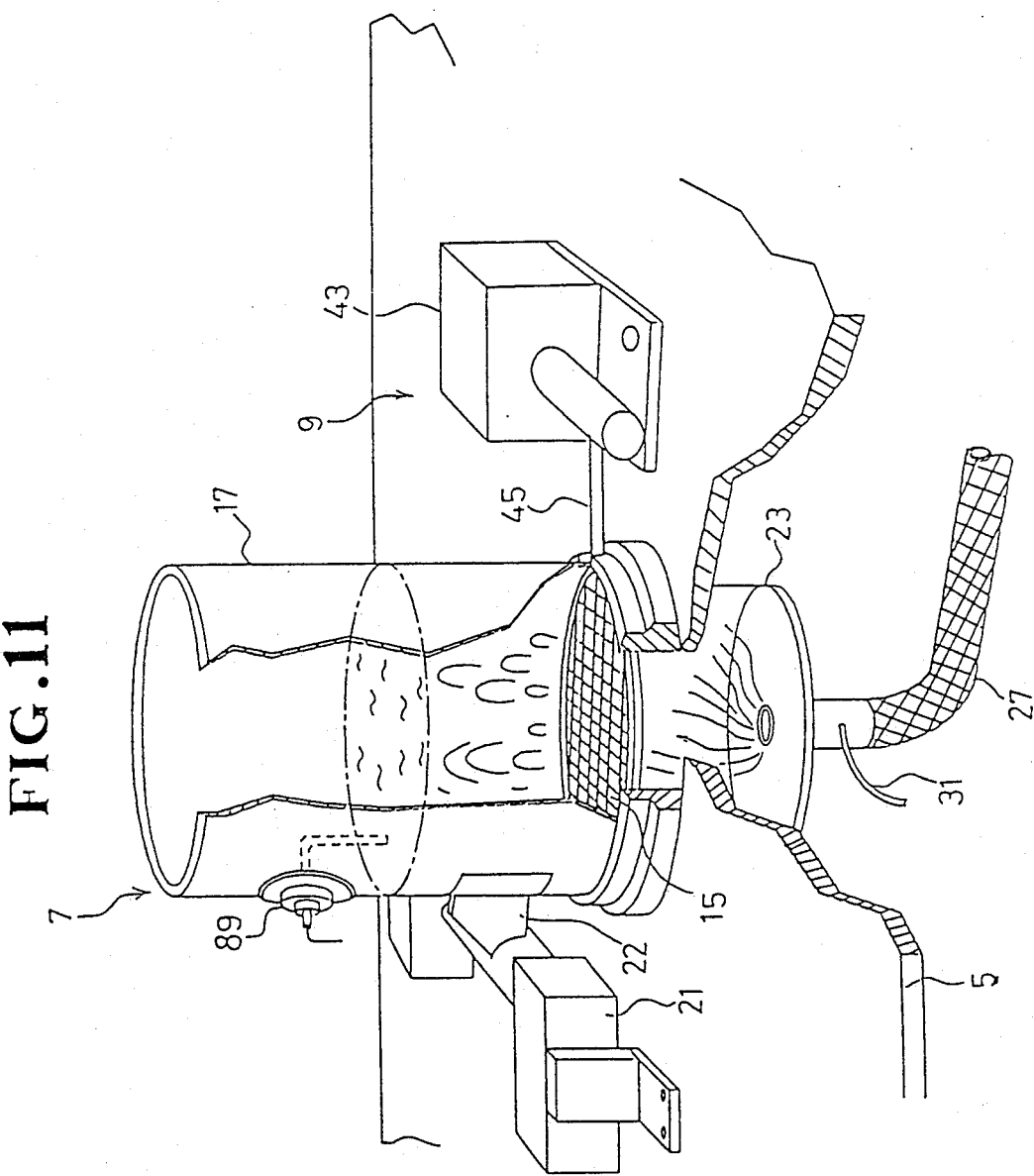
FIG. 11 is a perspective view of a wet sheet-like intermediate sample forming unit, with parts broken away for clarity, illustrating the unit in the stirring mode.

The wet sheet-like intermediate sample forming unit 7 includes, as shown in FIGS. 3 and 11, a filter 15 movably disposed over a circular opening in the table 3, and a stirring tank 17 disposed on the filter 15.

The filter 15 is composed of a circular fine wire net having an appropriate size, such as 100 mesh which is small enough to separate fiber contents from water, thereby forming a deposit of fiber contents on the filter 15 when the sampled dilute fiber suspension is poured out into the stirring tank 17. The shape and configuration and the material of the filter 15 are not limited to those shown in the illustrated embodiment.

The stirring tank 17 is in the form of a hollow cylinder and is detachably and sealingly fitted over an outer peripheral edge of the circular filter 15. The stirring tank 17 is connected to an operating arm 22 of a rotary actuator 21. The rotary actuator 21 is driven to move the stirring tank 17 between a vertical operating position in which the stirring tank 17 is fitted over the filter 15 as indicated by the solid lines in FIG. 3, and a tilted waiting position in which the stirring tank 17 is detached from the filter 15 as indicated by the phantom lines in the same figure. The stirring tank 17 is disposed in the tilted waiting position when a wet sheet-like intermediate sample 13 formed on the filter 15 is removed from the filter 15.

A cup-shaped suction tank 23 is disposed directly below the filter 15 and operatively connected with a vacuum pump 23 and an air compressor 26 that are disposed below the suction tank 23.

The suction tank 23 and the vacuum pump 25 are connected by a pipe 27 via a shutoff valve 28. The pipe 27 has an end connected to the bottom of the suction tank 23. The air compressor 26 has an air supply pipe 29 from which a small air supply pipe 31 is branched. The branched air supply pipe 31 is connected to the pipe 27 adjacent to the end thereof connected to the suction tank 23. The branched air supply pipe 31 has a shutoff valve 35.

When the sampled dilute fiber suspension poured out into the stirring tank 17 is to be stirred, the air compressor 26 is driven to supply a compressed air to the interior of the stirring tank 17 successively through the pipe 29, the pipe 31 and the pipe 27. When the stirring of the sampled dilute fiber suspension is completed, water in the dilute fiber suspension is drawn by filtration with vacuum. In this instance, the vacuum pump 25 is driven to withdraw the water from the suction tank 23 and the stirring tank 17 through the pipe 27. During that time, the operation of the air compressor 27 is interrupted. After completion of the vacuum dewatering, the air compressor 26 is driven again to supply a compressor air to the suction tank 23, the filter 15 and the stirring tank 17. The suction tank 23, the filter 15 and the stirring tank 17 restore their initial conditions.

The sample removing unit 10 is constructed as described below.

Figure 13:
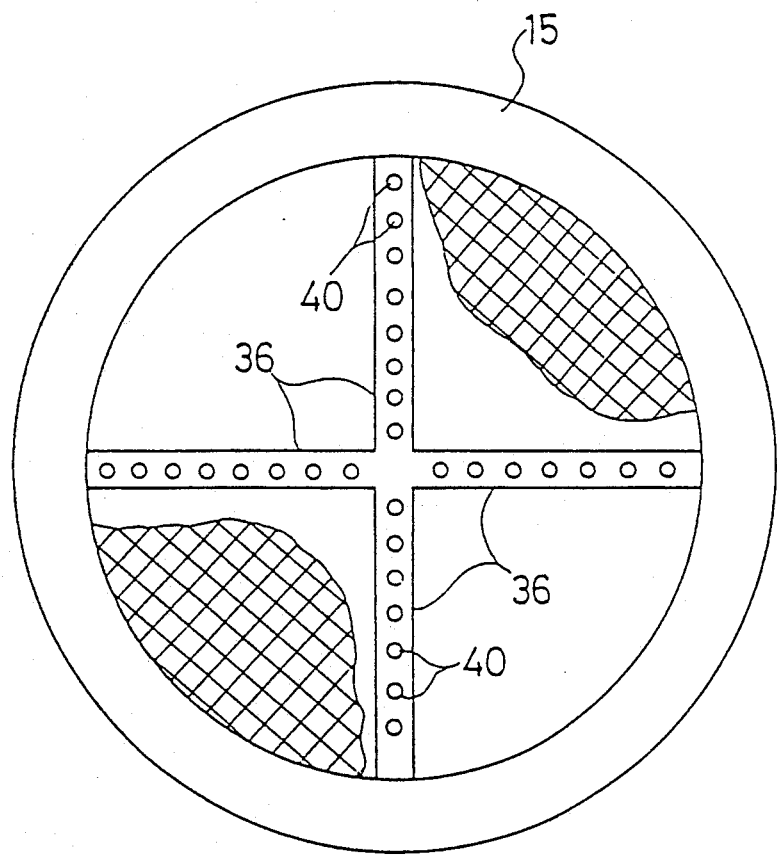
FIG. 13 is a plan view of a part of an overturning conveyor unit having a filter shown with parts broken away for clarity and a wet sample removing unit associated with the filter.

The air supply pipe 29 has another branched air supply pipe 33 across which a shutoff valve 37 is disposed. An air supply pipe in the form of a crisscross pipe 36 (FIG. 13) is disposed below the filter 15 and connected to a flexible air pipe 38 which in turn is connected to the branched air supply pipe 33 via a nozzle 39 formed in a peripheral wall of the suction tank 23. The crisscross air supply pipe 36 has a plurality of uniformly spaced air nozzles 40 facing upwardly so that a compressed air supplied through the air supply pipes 29, 33 and 38 to the crisscross air supply pipe 36 is ejected from the air nozzles 40 onto the underside of the wet sheet-like intermediate sample 13, thereby removing the intermediate sample 13 from the filter 15. Since the air nozzles 40 are spaced at substantially equal intervals, the compressed air is distributed uniformly over the surface of the wet intermediate sample 13. As a result, removal of the wet intermediate sample 13 can be effected smoothly without damaging the intermediate sample 13.

The removal of the intermediate sample 13 is achieved in subsequent to the overturning conveyance of the intermediate sample 13 by means of the overturning conveyor unit 9.

The overturning conveyor unit 9 includes a rotary actuator 43 disposed between the intermediate sample forming unit 7 and the dryer unit 11 and having an actuating arm 45 connected to the filter 15.

The rotary actuator 43 is driven to angularly move or turn the actuating arm 45 and the filter 15 concurrently about the axis of the actuating arm 45 through an angle of 180 degrees, so that the intermediate sample 13 formed on the filter 15 is conveyed from a stirring and suction station to a drying station. The intermediate sample 13, as it is transferred to the drying station, is inverted or turned upside down. The overturning conveyor unit 9 thus constructed is simple in construction and small in size and hence occupies only a small space for installation.

The dryer unit 11 comprises a hot press disposed at the drying station. The hot press is composed of an upper hot plate 47 fixedly mounted above the table 5, and a lower hot plate 49 disposed on the table 5 for supporting thereon the wet sheet-like intermediate sample.

The lower hot plate 49 is connected to a piston rod 53 of a shift cylinder 51. When the shift cylinder 51 is actuated to extend the piston rod 53, the lower hot plate 49 is moved upwardly toward the stationary upper hot plate 47 while the wet sheet-like intermediate sample 13 is held on the lower hot plate 49 so that the wet intermediate sample 13 is compressed by and between the upper and lower hot plates 47, 49.

Each of the upper and lower hot plates 47, 49 has an induction heater 11a, 11b (FIGS. 15A and 15B) incorporated therein and including an induction coil connected to an electric power supply (not shown) for heating the hot plate 47, 49. The temperature of the respective hot plates 47, 49 is controlled by thermostat. The induction heater 11a, 11b may be incorporated in at least one of the upper and lower hot plates 47, 49.

In the illustrated embodiment, the dryer unit 11 employs an induction heating system. When energized, the induction coil produces an electromagnetic flux. The electromagnetic flux, as it passes through metal plates attached to end edges of the hot plate 47, 49, is converted into eddy-current induced in the metal plates. Then the metal plates generate heat, thereby heating the hot plates 47, 49 and the wet sheet-like intermediate sample 13 compressed between the upper and lower hot plates 47, 49. The wet intermediate sample 13 is thus dried with heat and pressure. The induction heating system may be replaced by a microwave heating system or an electric heating system.

Figure 15A:
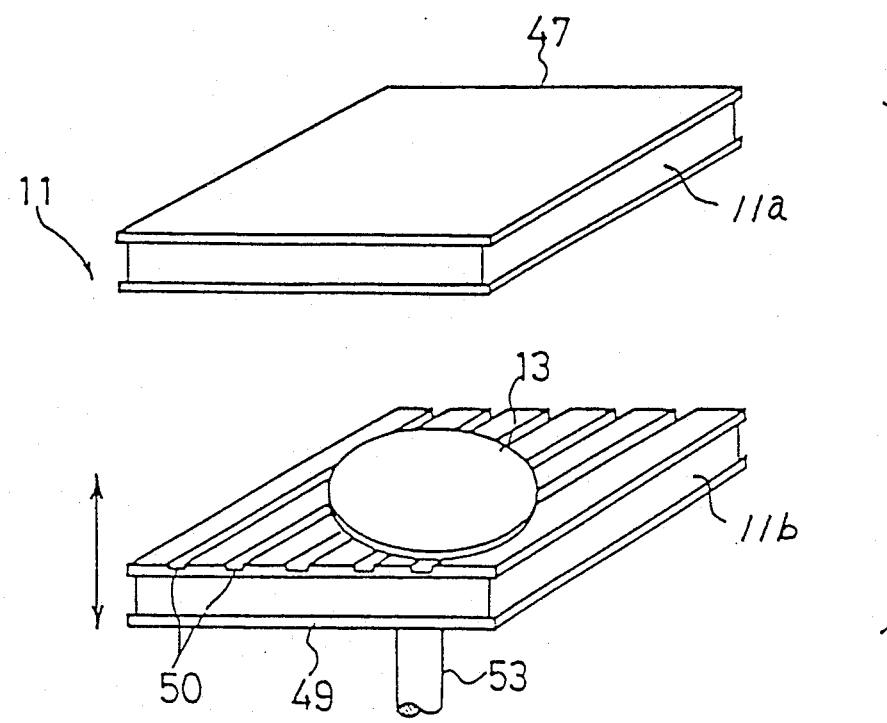
FIGS. 15A and 15B are perspective views illustrative of the operation of a hot press having a cooperating pair of hot plates.
Figure 15B:
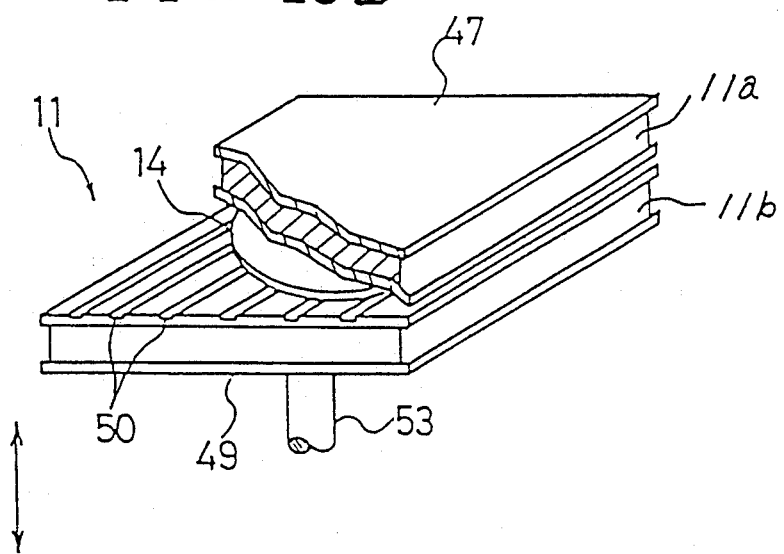
Figure 21:
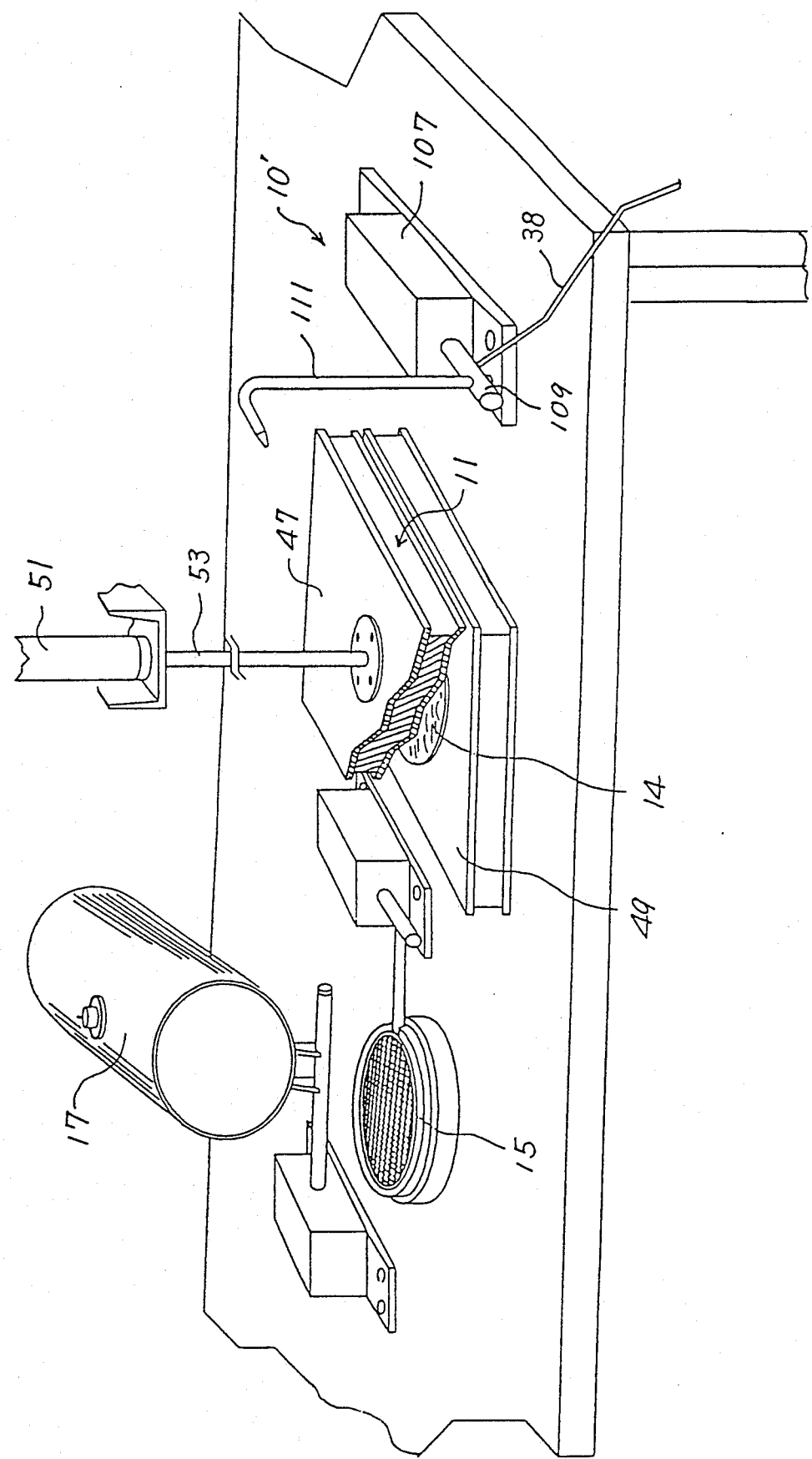

As shown in FIGS. 15A and 15B, the upper surface of the lower hot plate 49 has a plurality of parallel spaced grooves 50. The grooves 50 permit water vapor to escape through the grooves 50 to the outside of the hot press while the wet intermediate sample 13 is being heated. With the grooves 50 thus provided, the heating efficiency is increased and the necessary heating time is reduced. The upper hot plate 47 may have similar grooves. The number, size and configuration of the grooves 50 are not limited to those of the illustrated embodiment. Furthermore, the upper hot plate 47 may be vertically movable in which instance the lower hot plate 49 is stationary and the shift cylinder 51 is connected to the upper hot plate 47 for reciprocating the same with respect to the stationary lower hot plate 49, as shown in FIG. 21.

Figure 16:
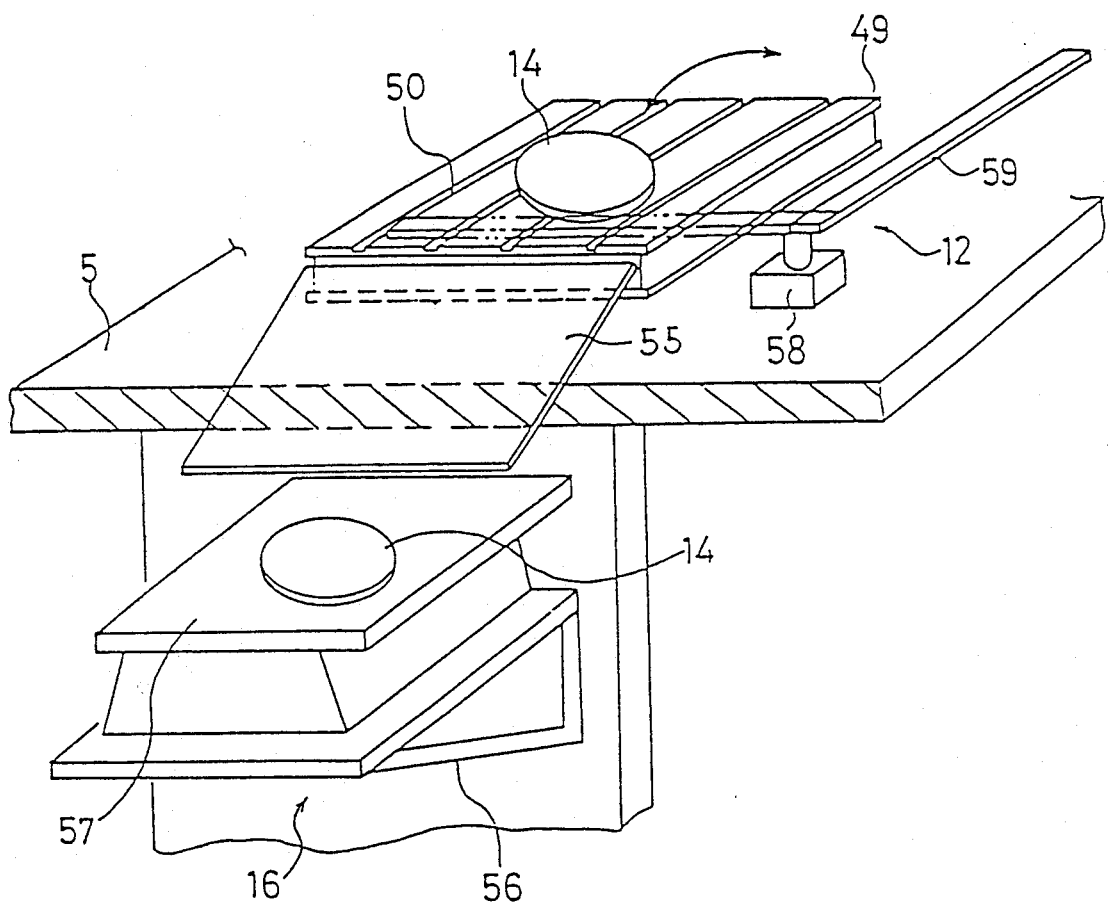
FIG. 16 is a perspective view showing a weighing unit and a dry sample transfer unit associated therewith.

As best shown in FIGS. 3 and 16, the transfer unit 12 is disposed adjacent to the lower hot plate 49 for feeding a dry sheet-like final sample 14 from the dryer unit 11 onto the weighing unit 16 via a chute 55. The chute 55 is disposed adjacent to the downstream end of the lower hot plate 49.

The weighing unit 16 includes an electronic weighing scale 57 mounted on a bracket 56 attached to the frame 1 (FIG. 3). The transfer unit 12, as shown in FIG. 16, includes a rotary actuator 58 having an actuating arm 59 pivotally movable in a horizontal plane lying immediately above the upper surface of the lower hot plate 49 so that the final sample 14 is displaced from the lower hot plate 49 onto the chute 55. Subsequently, the final sample 14 falls down along the chute 55 onto the electronic weighing scale 57 of the weighing unit 16.

Figure 6:
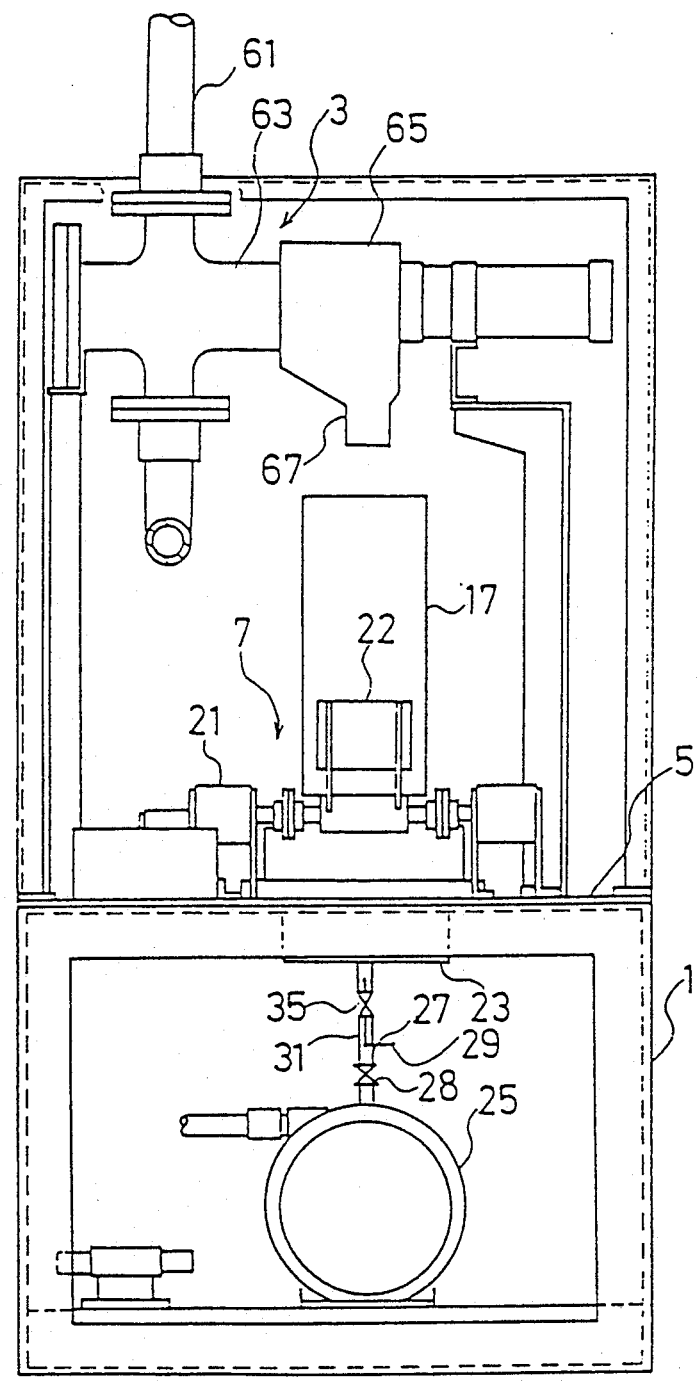
FIG. 6 is a view taken in the direction f the arrows along the line VI—VI of FIG. 3.

The sampling unit 3 will be described below in greater detail with reference to FIGS. 6, 7 and 8.

The pulp liquor to be measured for its pulp concentration flows through a main pipe 61. The main pipe 61 has a branched pipe 63 to which a hopper 65 is connected. The hopper 65 has at its lower end a discharge hole 67 disposed adjacent to an upper end of the stirring tank 16 when the stirring tank 16 is disposed in its vertical operating position. The main pipe 61 may be replaced with a storage tank in which a dilute fiber suspension is retained.

Figure 7:
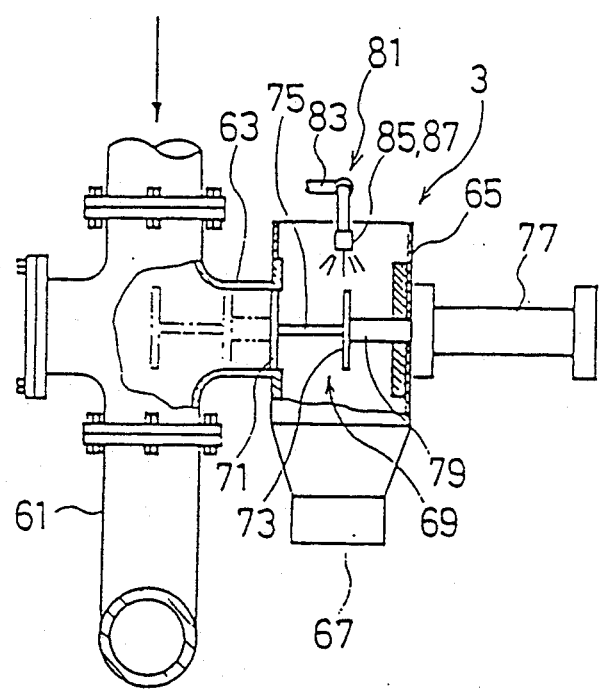
FIG. 7 is a fragmentary cross-sectional view of a sampling unit with parts broken away for clarity.
Figure 8:
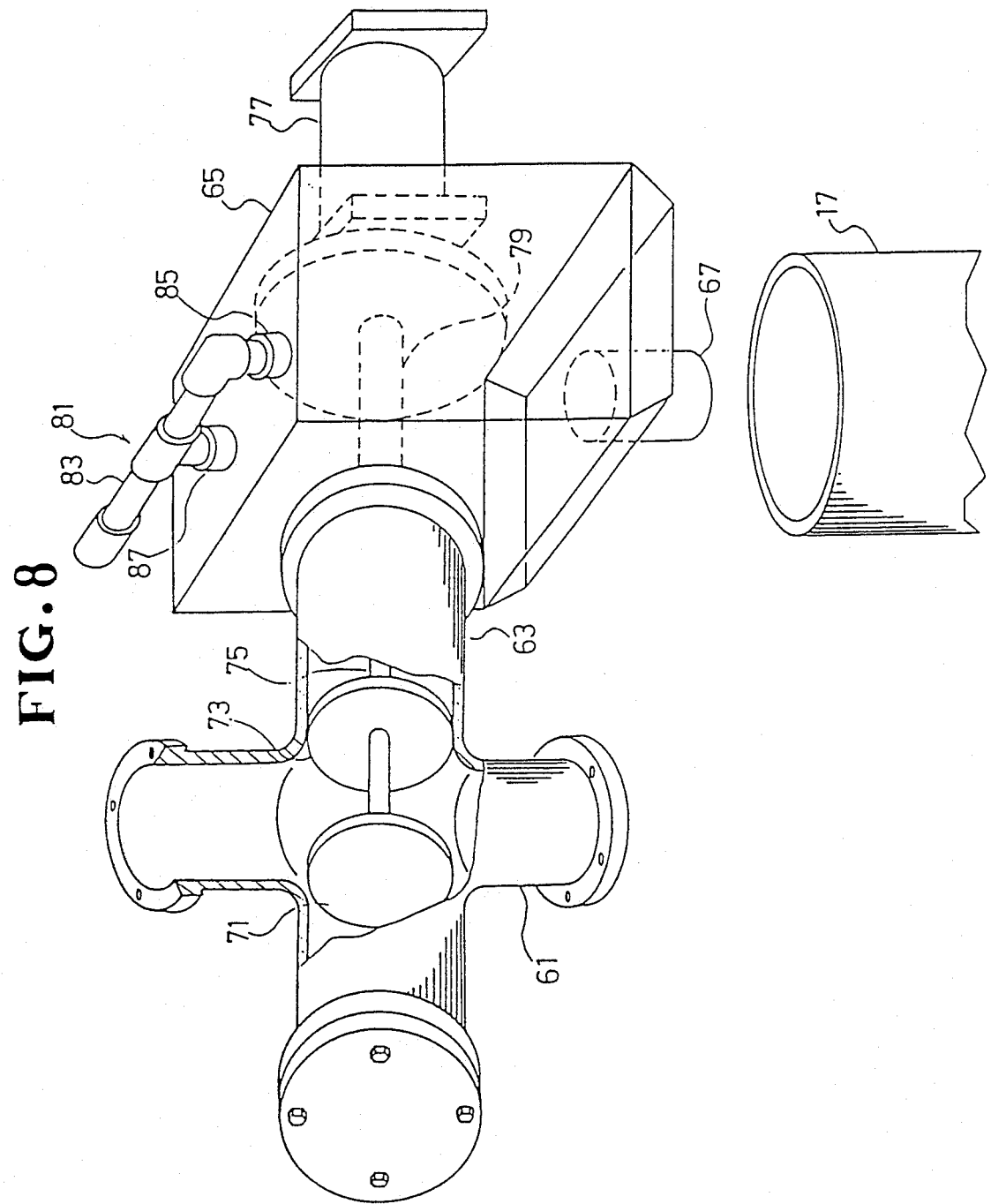
FIG. 8 is an enlarged perspective view of the sampling unit with parts broken away for clarity.

As shown in FIGS. 7 and 8, the hopper 65 houses therein a sampling mechanism 69 which includes a pair of parallel spaced circular plates 71, 73 connected together by means of a horizontal shaft 75. The circular plates 71, 73 have a same outside diameter which is slightly smaller than the inside diameter of the branched pipe 63 so that the circular plates 71, 73 are slidably movable along the branched pipe 63.

A shift cylinder 77 (FIG. 7) is disposed on the outside of the hopper 65 and has a piston rod 79 extending into the internal space of the hopper 65 and connected concentrically to the horizontal shaft 75.

When the shift cylinder 77 is actuated to reciprocate the shaft 75 via its piston rod 79, the plates 71, 73 are movable between the main pipe 61 and the hopper 65. With this reciprocating movement of the plates 71, 73, a part of the dilute fiber suspension is trapped between the plates 71, 73 and collected into the hopper 65. The collected dilute fiber suspension is thereafter poured out into the stirring tank 17.

The quantity of the collected or sampled dilute fiber suspension is determined depending on the space between the two plates 71, 73 so that a desired quantity of dilute fiber suspension can be collected by properly adjusting the spacing between the plates 71, 73.

The sampling mechanism 69 is associated with a water sprinkling mechanism 81 disposed on the upper end of the hopper 65. The water sprinkling mechanism 81 includes a water supply pipe 83 and a pair of water sprinkling nozzles 85, 87 branched from the water supply pipe 83 and disposed within the hopper 65.

With the water sprinkling mechanism 81 thus constructed, water is sprinkled over the inside surface of the hopper 65 and the outside surfaces of the moving parts 71, 73, 75 of the sampling mechanism 69, thereby washing away or removing the dilute fiber suspension adhering to the hopper 65 and the moving parts 71, 73, 75. The removed dilute fiber suspension is discharged from the hopper 65 through the discharge hole 67 and loaded into the stirring tank 17.

As shown in FIG. 3 and 11, a level sensor 89 is disposed within the stirring tank 17 for detecting the level of the dilute fiber suspension retained in the stirring tank 17 to thereby control on-off operation of the sprinkling mechanism 81 in such a manner to prevent overflow of the dilute fiber suspension.

The pulp concentration measuring apparatus of the foregoing construction operates as follows.

Figure 2:
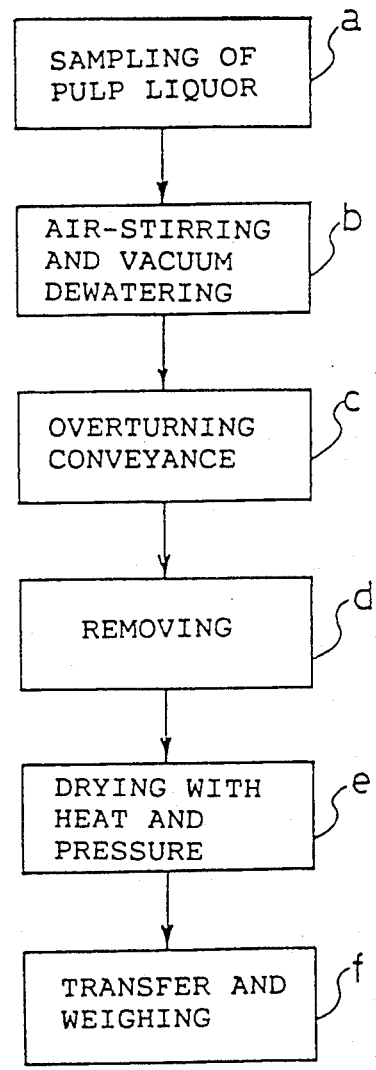
FIG. 2 is a block diagram showing the sequence of processing steps achieved in a method of measuring the pulp concentration of a dilute fiber suspension.

The operation begins from a sampling step as designated by "a" in FIG. 2.

In the sampling step "a", the shift cylinder 77 (FIG. 7) is actuated to reciprocate the shaft 75, thereby moving the plates 71, 73 into and out of the main pipe 61 whereupon a predetermined quantity of dilute fiber suspension is sampled into the hopper 65. The sampled dilute fiber suspension is supplied from the discharge hole 67 into the stirring tank 17. During that time, the water sprinkling mechanism 81 is driven to sprinkle water into hopper 65. With this water sprinkling, the dilute fiber suspension adhering to the outer surfaces of the plates 71, 73 and the shaft 75 and also on the inside surface of the hopper 65 is washed away and falls into the stirring tank 17 together with the sprinkled water.

When a dilute fiber suspension loaded in the stirring tank 17 reaches a predetermined level, the level sensor 89 issues a command signal to interrupt sprinkling operation of the water sprinkling mechanism 81.

Then the operation proceeds to a wet sheet-like intermediate sample forming step as designated by "b" in FIG. 2.

At the beginning of the intermediate sample forming step "b", the pulp liquor fills the internal space of the stirring tank 17 and the internal space of the suction tank 23 disposed below the stirring tank 17 with the filter 15 disposed between the tanks 17 and 23.

Then, a compressed air produced by the air compressor 26 is supplied through the pipes 29, 31, 27 into the suction tank 23 and the stirring tank 17 across the filter 15, as shown in FIG. 11. Consequently, the dilute fiber suspension is uniformly stirred by the compressed air and hence fiber contents are uniformly dispersed in water.

Figure 12:
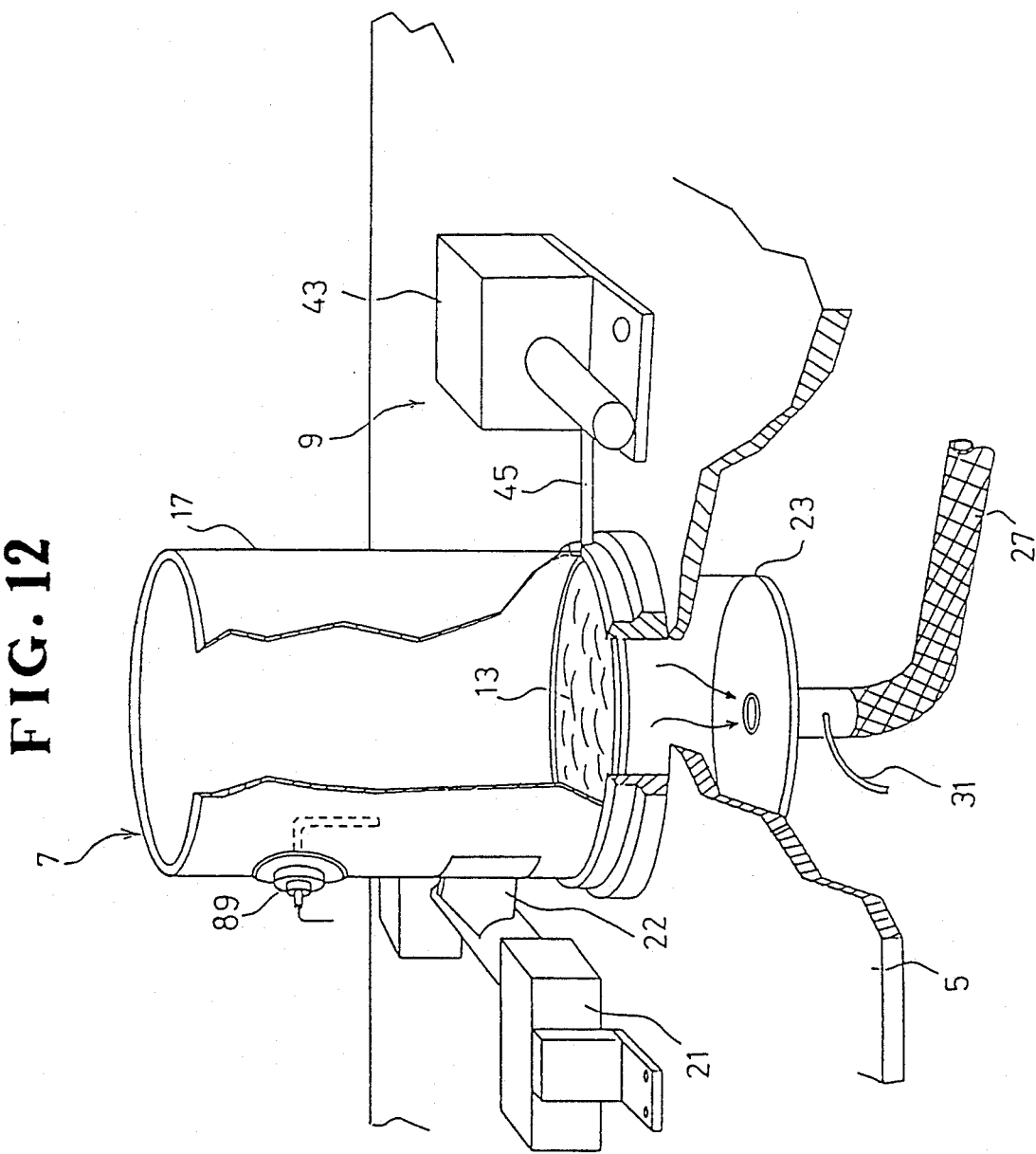
FIG. 12 is a view similar to FIG. 11, but showing the wet sheet-like intermediate sample forming unit in the dewatering mode.

Thereafter, the vacuum pump 25 is energized to draw the water contents in the dilute fiber suspension through the pipe 27. With this vacuum dewatering, the water contents are completely removed from the tanks 17, 23 while fiber contents are deposited uniformly over an upper surface of the filter 15, as shown in FIG. 12. The fiber contents thus deposited form a sheet-like intermediate sample 13 having a substantially uniform thickness. The intermediate sample 13 is dewatered to a certain extent but still wet.

Then, the vacuum pump 25 is de-energized and the compressed air is supplied again from the air compressor 26 to the suction tank 23 and the stirring tank 17 to release the vacuum state in the tanks 17, 23.

The foregoing intermediate sample forming step "b" is followed by an overturning conveyance step "c" such as designated by "c" in FIG. 2.

Figure 14:
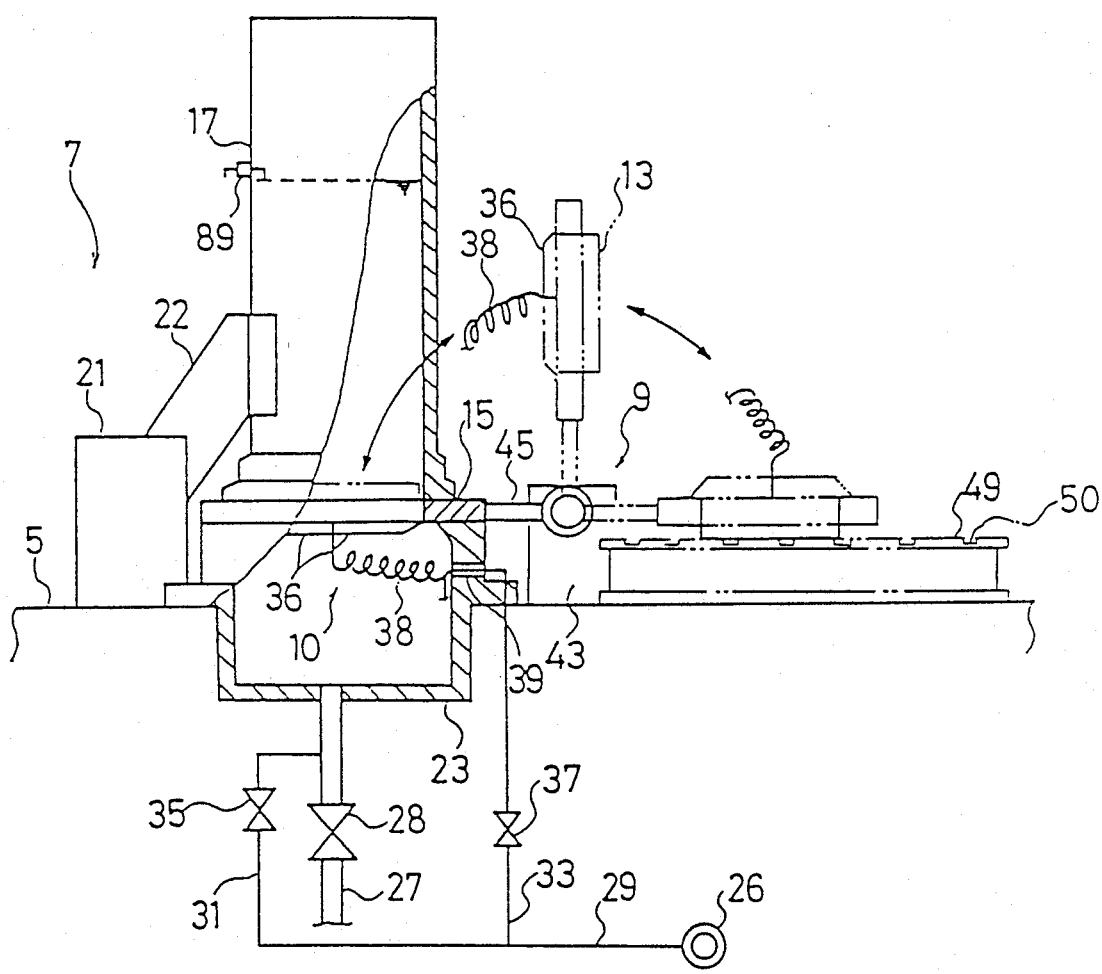
FIG. 14 is a front elevational, partly cross-sectional view illustrating the operation of the overturning conveyor unit.

In the overturning conveyance step "c", the stirring tank 17 is retracted into a tilted waiting position as indicated by the phantom lines in FIG. 3. Then, the rotary actuator 43 is driven to pivot the actuating arm 45 about its proximal end through an angle of 180 degrees, thereby causing the filter 15 to turn through an angle of 180 degrees. With this angular movement of the filter 15, the wet sheet-like intermediate sample 13 is turned upside down and transferred to the lower hot plate 49 of the dryer unit 11, as shown in FIG. 14. Since the filter 15 is turned upside down, the intermediate sample 13 is held in direct contact with the upper surface of the lower hot plate 49.

A sample removing step as designated by "d" in FIG. 2 follows the overturning conveyance step "c" described above.

In the sample removing step "d", a compressed air is suppled successively through the pipe 29, the pipe 33, the nozzle 39, and the flexible pipe 38 to the crisscross pipe 36 and then ejected downwardly from the nozzles 40 against the upper surface of the intermediate sample 13. With this compressed air thus supplied, the intermediate sample 13 is removed from the filter 15.

The rotary actuator 43 is driven again to return the filter 15 to its initial position.

The foregoing sample removing step "d" is followed by a drying step designated by "e" in FIG. 2.

In the drying step "e", the shift cylinder 51 is actuated to move the lower hot plate 49 toward the stationary upper hot plate 47 while the sheet-like intermediate sample 13 is supported on the lower hot plate 49.

Thus, the wet sheet-like intermediate sample 13 is sandwiched between the upper and lower hot plates 47, 49, as shown in FIG. 15B. The wet intermediate sample 13 is dried by heating with the hot plates 47, 49. During that time, water vapor is allowed to escape through the grooves 50 and, therefore, the heating efficiency is substantially improved and the necessary heating time can be reduced.

The wet intermediate sample is compressed by the upper and lower hot plates 47, 49 at a pressure of 5 kg/cm$^2$, for example. The upper and lower hot plates 47, 49 are heated at about 140° C.

When a predetermined heating time period elapses, the lower hot plate 49 is lowered to its initial position. Then the operation proceeds to a transfer and weighing step such as designated by "f" in FIG. 2.

In the transfer and weighing step "f", the rotary actuator 58 is driven to turn the actuating arm 59 from the solid-lined position to the phantom-lined position, thereby forcing a dry sheet-like final sample 14 from the lower hot plate 49 toward the chute 55. Then, the final sample 14 slides down along the chute 55 and falls onto the electronic weighing scale 57 of the weighing unit 12, as shown in FIG. 16. The weighing scale 57 measures an oven-dry weight of the dry final sample 14. The thus-measured oven-dry weight and a previously measured total weight of the sampled dilute fiber suspension are used to calculate the pulp concentration of the dilute fiber suspension.

As described above, the apparatus of the present invention is capable of measuring the pulp concentration automatically. Such automatic pulp concentration measurement obviates the need for laborious manual operation and requires only a short period of measuring time.

Figure 1:
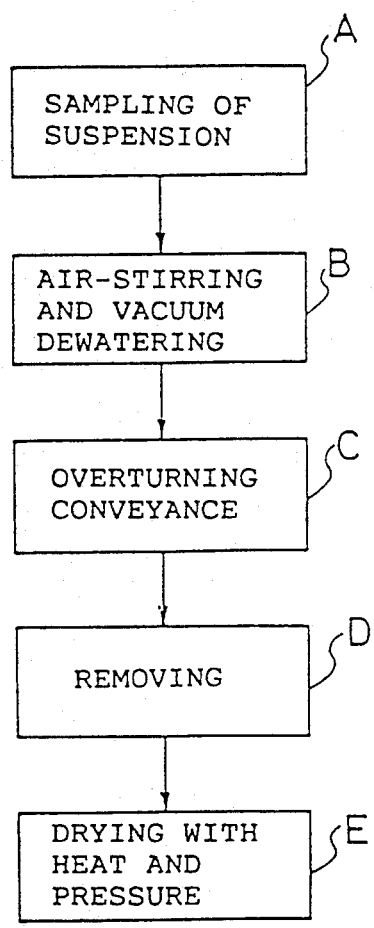
FIG. 1 is a block diagram showing the sequence of processing steps achieved in a method of making a dry sheet-like sample of solid particles from a suspension according to the present invention.

The present invention is not limited to the foregoing embodiment and it is also useful when embodied in a method of making a dry sheet-like sample of solid particles from a suspension, such as shown in FIG. 1. The dry sample making method shown in FIG. 1 includes a series of processing steps A-E which are substantially the same as those "a"-"e" of the pulp concentration measuring method shown in FIG. 2 with the exception that the transfer and weighing step "f" is no longer necessary in the dry sample making method shown in FIG. 1. The dry sample may be used for a measurement of ash content in which the dry sample undergoes subsequent burning, a color analysis of fiber contents, and various measurements and analyses other than specified above.

Figure 9:
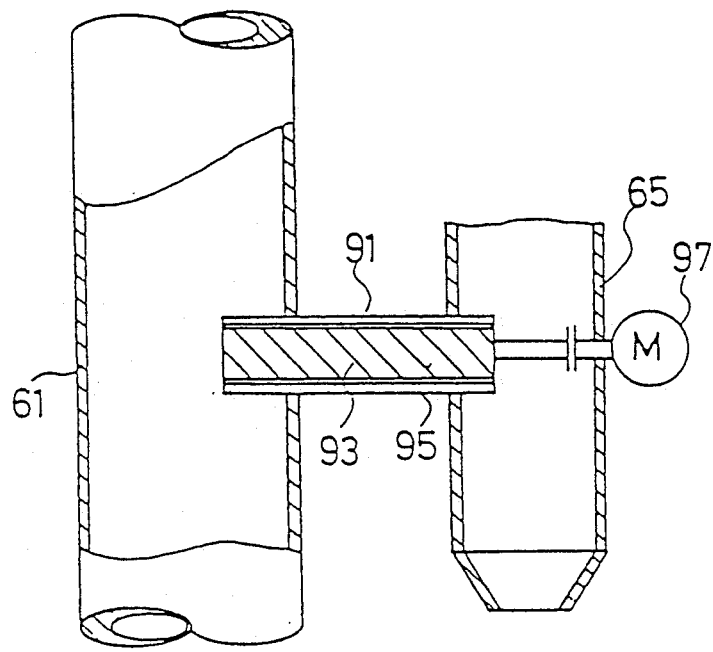
FIG. 9 is a cross-sectional view of a modified sampling unit.

FIG. 9 shows a modified form of the sampling unit. The modified sampling unit includes a sampling mechanism in the form of a screw pump. The screw pump includes a shaft 95 having a helical screw blade 93 and rotatably received in a branched pipe 91 extending between the main pipe 61 and the hopper 65. The shaft 95 is coupled with a drive motor 97 disposed on the outside of the hopper 65.

Figure 10:
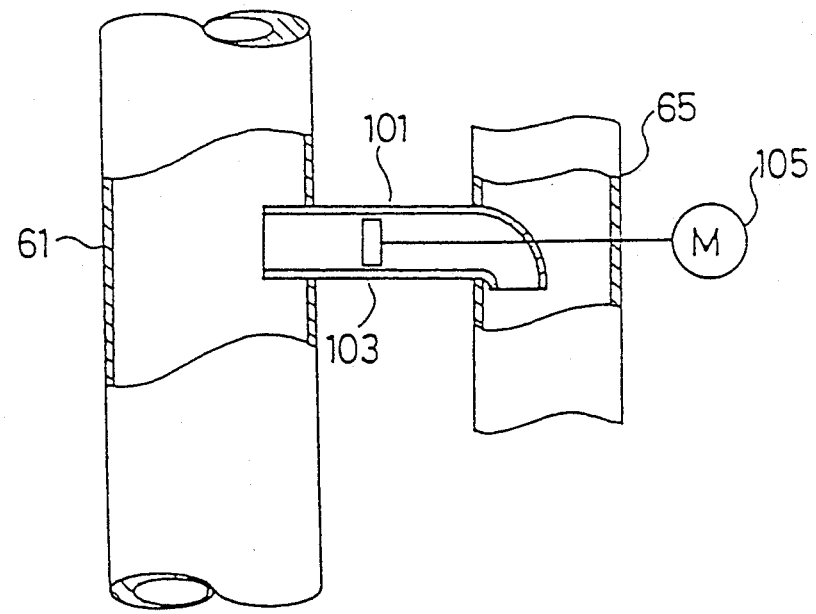
FIG. 10 is a view similar to FIG. 9, but showing another sampling unit.

FIG. 10 illustrates another modified sampling unit which employs an axial flow pump. The axial flow pump sampling unit includes an impeller 103 rotatably disposed in a branched pipe 101 extending from the main pipe 61 to the hopper 65, and a drive motor 105 connected to the impeller 103 for rotating the same.

Other sampling units replaceable with any of the sampling units specified above include a screw conveyor and a suction sampling unit.

Figure 17:
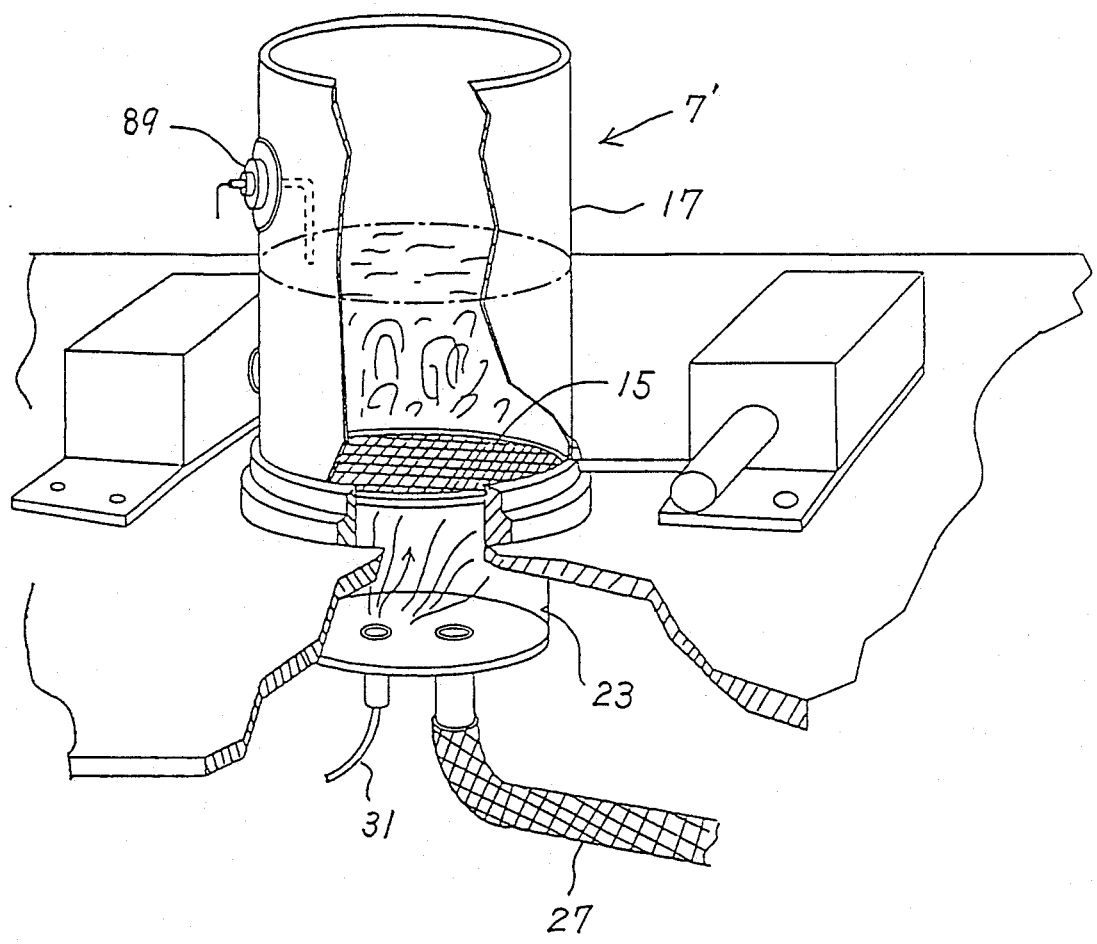
FIGS. 17 and 18 are views similar to FIGS. 11 and 12, respectively, but showing a modified wet sheet-like intermediate sample forming unit.
Figure 18:
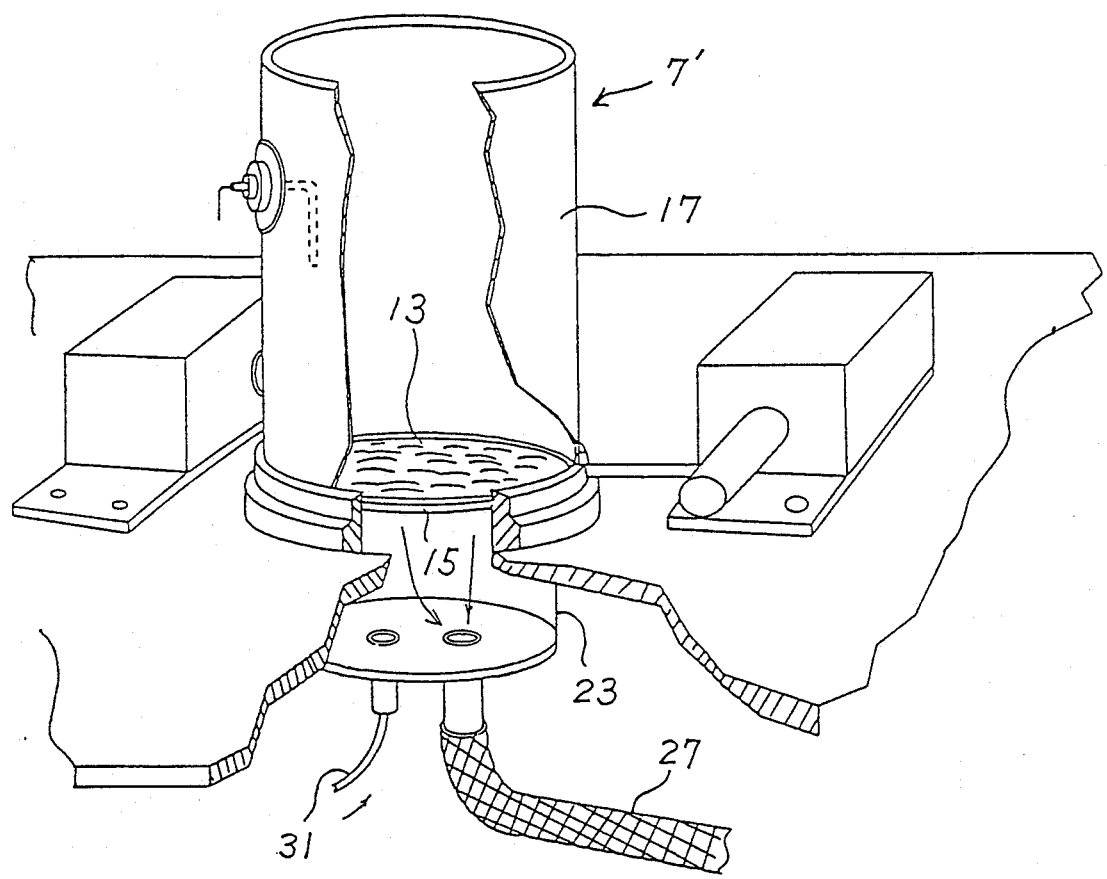

FIGS. 17 and 18 show a modified wet intermediate sample forming unit 7' according to the invention. The modified sample forming unit 7' differs from the sample forming unit 7 of the foregoing embodiment shown in FIGS. 11 and 12 in that the branched air supply pipe 31 is directly connected to the bottom of the suction tank 23.

Figure 19:
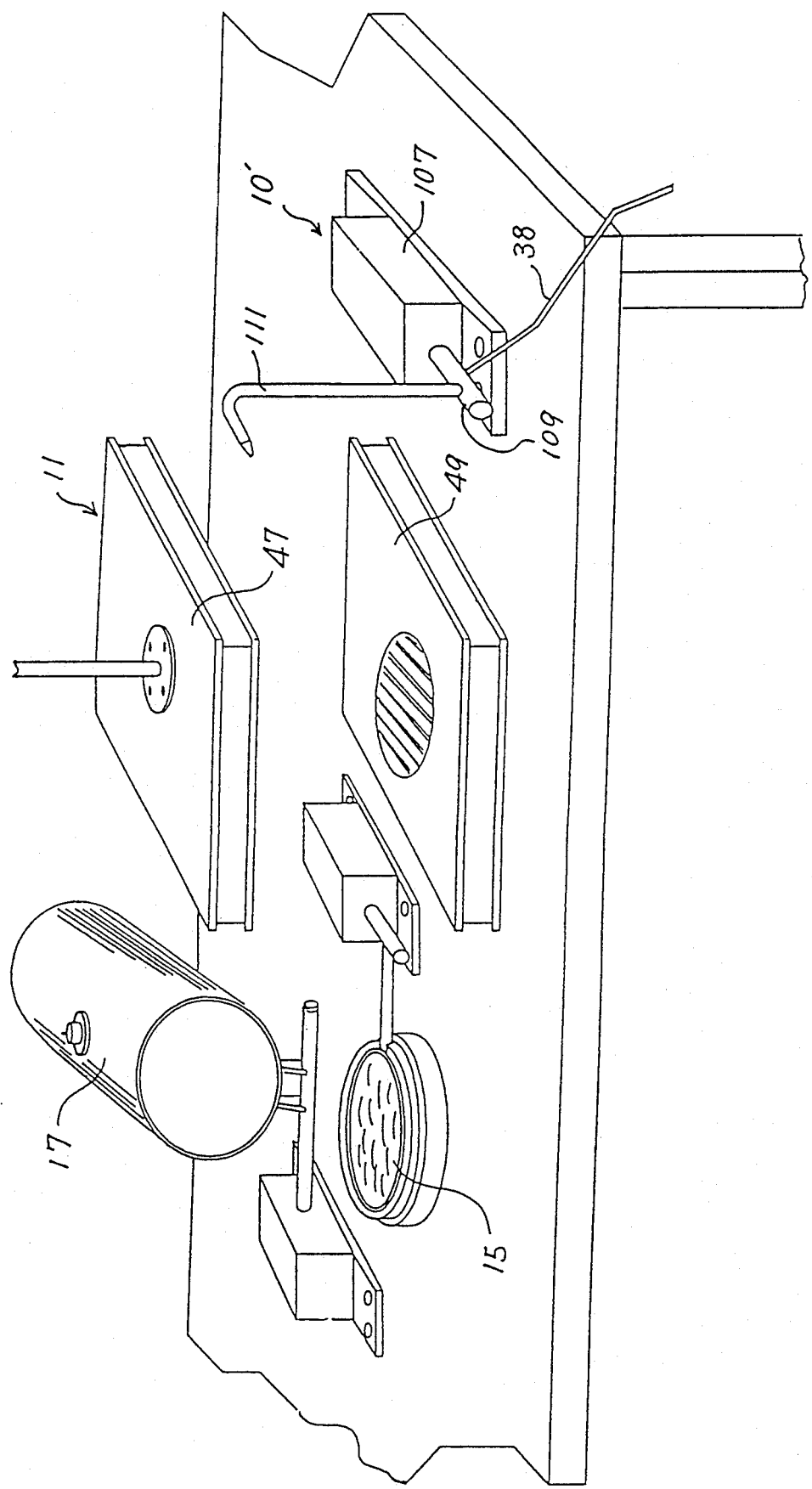
FIGS. 19, 20 and 21 are perspective views showing the operation of a modified sample removing unit.
Figure 20:
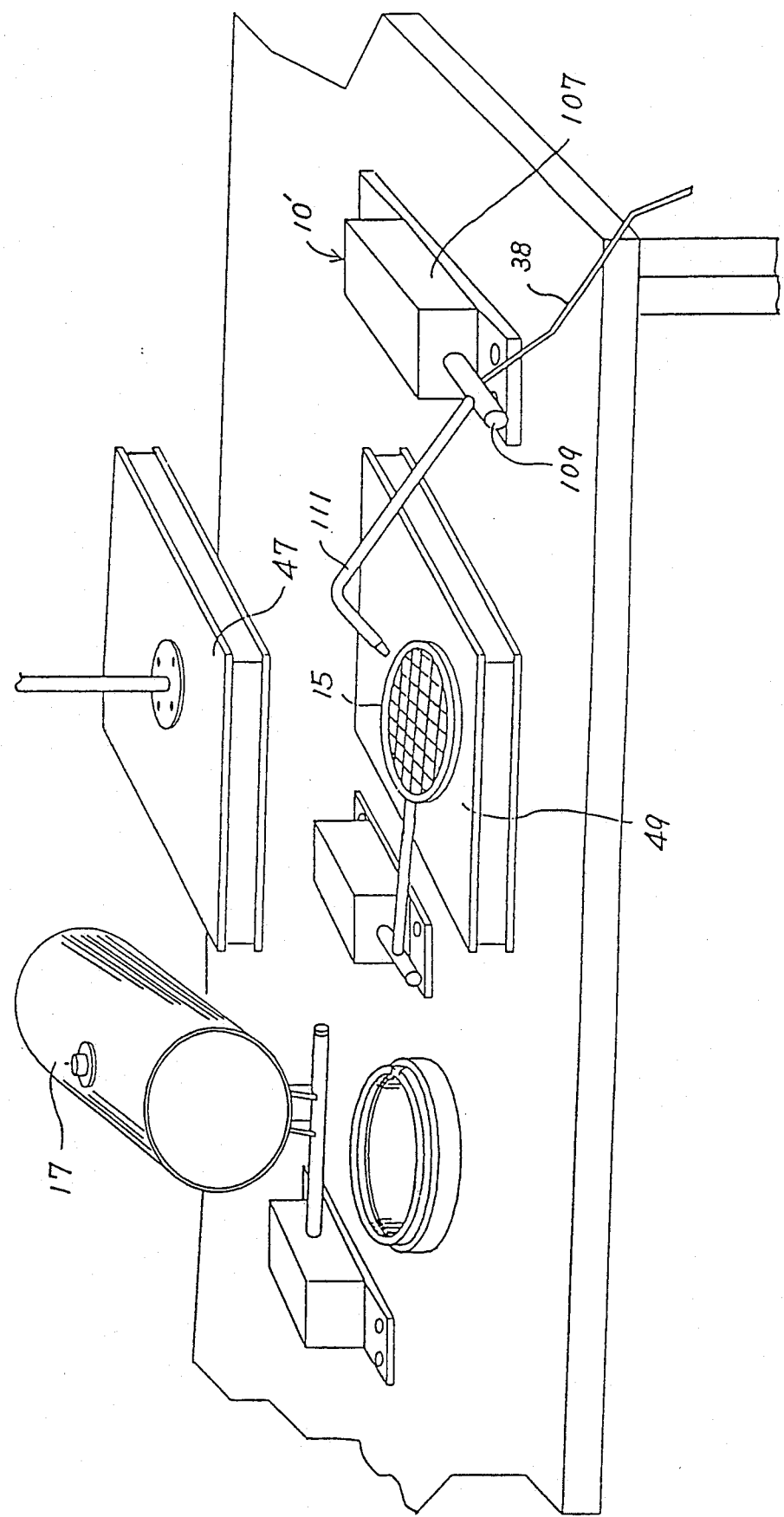

FIGS. 19 through 21 illustrate a modified sample removing unit 10' which comprises a rotary actuator 107 having a drive shaft 109, and an elongate nozzle 111 connected to the drive shaft 109. In response to the operation of the rotary actuator 107, the nozzle 111 is angularly movable between a vertical waiting position (FIGS. 19 and 21) remote from the dryer unit 11, and a tilted operating position (FIG. 20) adjacent to the upper side of the filter 15 as the filter 15 is disposed on the lower hot plate 49. When the nozzle 111 is disposed in its operating position shown in FIG. 20, a compressed air supplied from the air compressor 26 (FIG. 3) is ejected from the nozzle 111 against the upper side of the filter 15, thereby removing a wet intermediate sample 13 (FIG. 21) from the filter 15.

Figure 22:
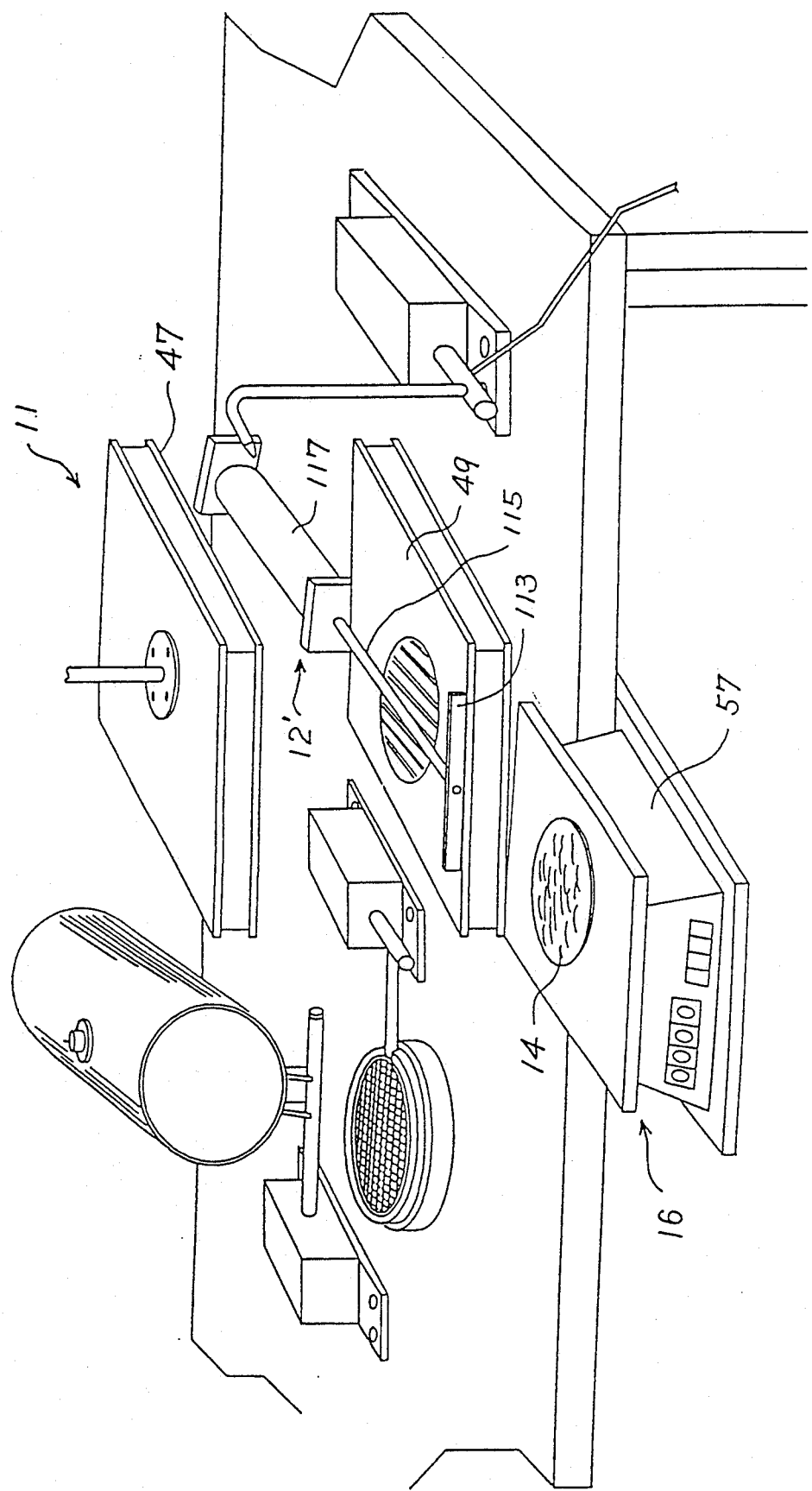
FIG. 22 is a perspective view of a dry sample transfer unit according to another embodiment.

A modified dry sample transfer unit 12' shown in FIG. 22 differs from the dry sample transfer unit 12 shown in 16 in that a transverse pusher bar 113 connected to a piston rod 115 of a shift cylinder 117 reciprocates along the upper surface of the lower hot plate 49 in response to the operation of the shift cylinder 117 so that a dry final sample 14 is transferred from the dryer unit 11 to an electronic weighing scale 57 of the weighing unit 16 disposed adjacent to the lower hot plate 49.

Obviously various minor changes and modifications of the present invention are possible in the light of the above teaching. It is therefore to be understood that within the scope of the appended climes the invention may be practiced otherwise than as specifically described.

What is claimed is:

1. A method of making a dry sheet-like sample of solid particles from a suspension, comprising the steps of:
   (a) sampling a part of the suspension as it flows through a pipe or while it is retained in a storage tank
   (b) stirring the thus-sampled suspension by supplying compressed air to the sampled suspension and then dewatering the stirred suspension on a filter by filtration with vacuum, thereby forming a wet sheet-like intermediate sample of solid particles deposited on the filter;
   (c) conveying the filter and the wet sheet-like intermediate sample deposited thereon to a drying station comprising an upper hot plate and a lower hot plate movable toward and away from each other, while turning the filter and the wet sheet-like intermediate sample upside down onto the lower hot plate of the drying station, and subsequently removing the wet sheet-like intermediate sample from the filter; and
   (d) thereafter, drying the wet sheet-like intermediate sample with heat and pressure in the drying station, thereby forming a dry sheet-like final sample.

* * * * *